United States Patent [19]
Shiu

[11] Patent Number: 5,098,412
[45] Date of Patent: Mar. 24, 1992

[54] SUPPORT SYSTEM FOR CATHETER

[76] Inventor: Man F. Shiu, 39 Dyott Road, Moseley, Birmingham B13 9OZ, England

[21] Appl. No.: 607,511

[22] Filed: Nov. 1, 1990

[30] Foreign Application Priority Data

Nov. 4, 1989 [GB] United Kingdom ............... 8924946

[51] Int. Cl.$^5$ ........................................... A61M 27/00
[52] U.S. Cl. .................................... 604/280; 604/95; 604/284; 128/772
[58] Field of Search ................... 128/772; 604/93, 96, 604/171, 263–264, 274, 280, 282, 284, 95

[56] References Cited

U.S. PATENT DOCUMENTS

| 4,405,313 | 9/1983 | Sisley et al. | 604/43 |
| 4,674,495 | 6/1987 | Orr | 604/93 X |
| 4,748,984 | 6/1988 | Patel | 128/658 |
| 4,813,930 | 3/1989 | Elliott | 604/53 |
| 4,925,452 | 5/1990 | Melinyshyn et al. | 604/284 |

Primary Examiner—C. Fred Rosenbaum
Assistant Examiner—Corrine Maglione
Attorney, Agent, or Firm—Ware, Fressola, Van Der Sluys & Adolphson

[57] ABSTRACT

A support system for a guiding catheter used in coronary treatment such as percutaneous transluminum coronary angioplasty (PTCA) includes a main lumen, a secondary lumen and a linearly incompressible flexible elongate element slidable within the secondary lumen. The main and secondary lumen are connected integrally together throughout the proximal portion of the length of the catheter but are separated throughout a distal portion, the elongate element, which may be a wire or metal strip, being anchored at the distal end of the catheter. The proximal end of the catheter includes operating means to exert endwise force on the elongate element and to cause the separated portion of the secondary lumen to move away from the main lumen so as to brace the catheter against opposed walls of a vessel to retain it in position. When the catheter has been braced against the vessel walls, a PTCA procedure can be carried out.

10 Claims, 3 Drawing Sheets

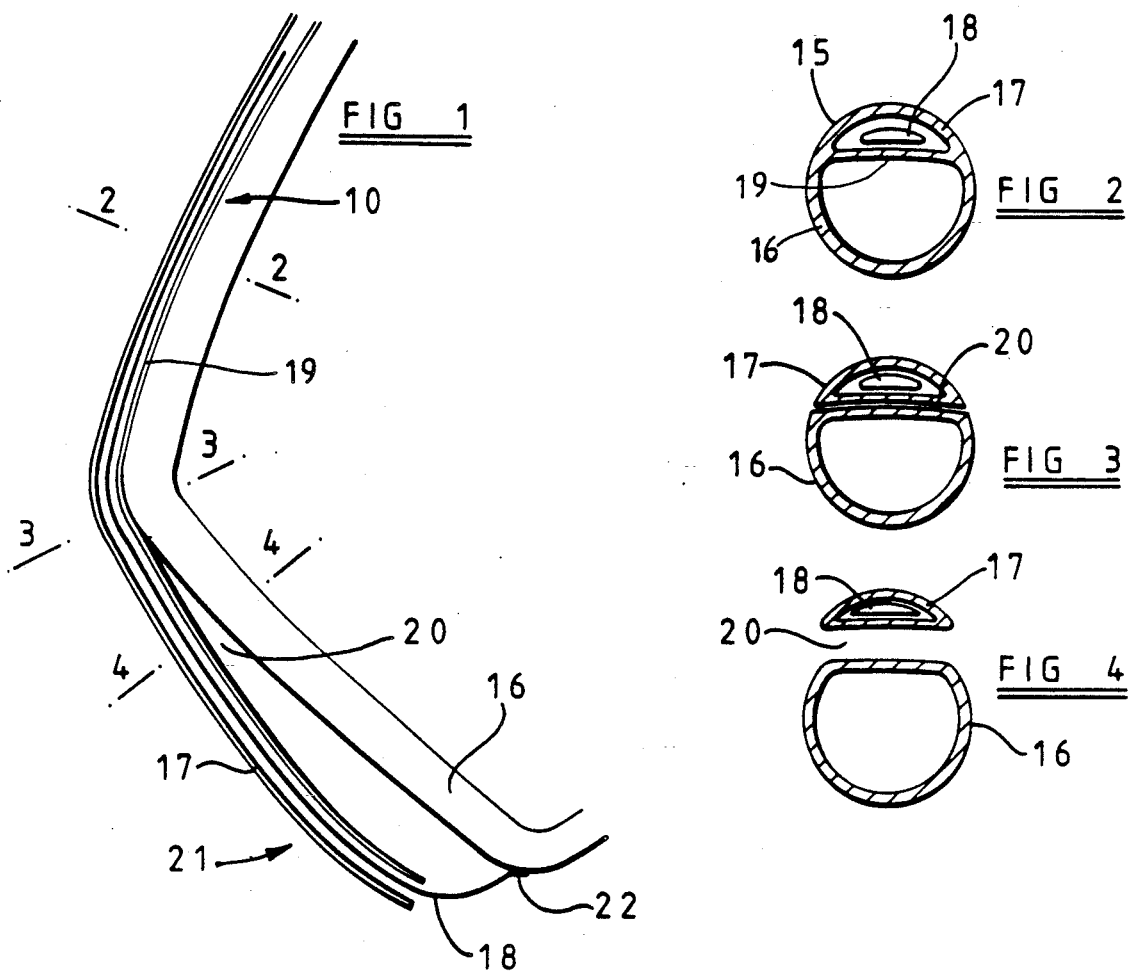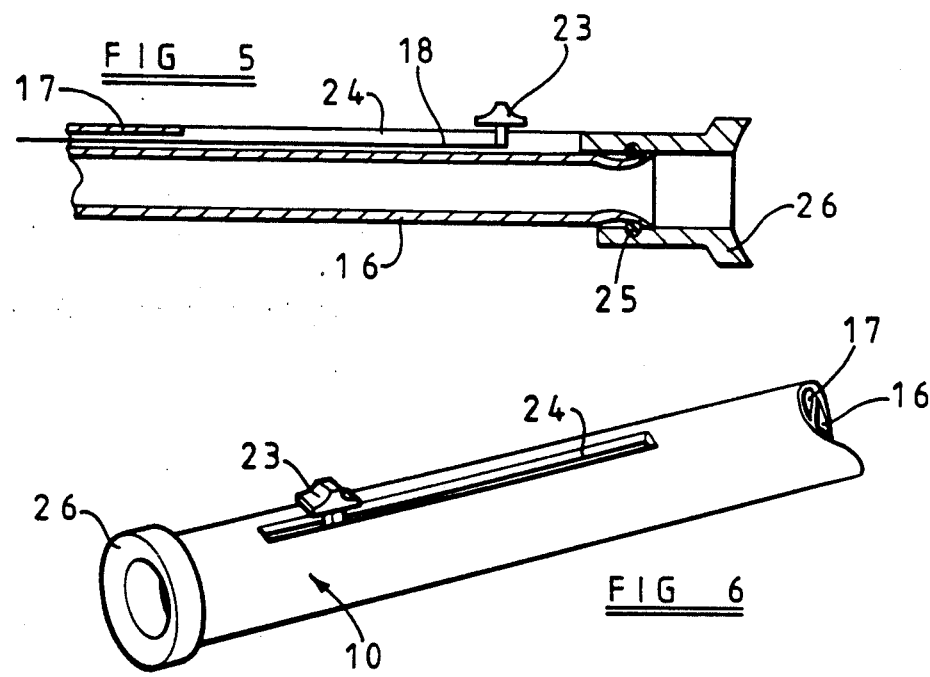

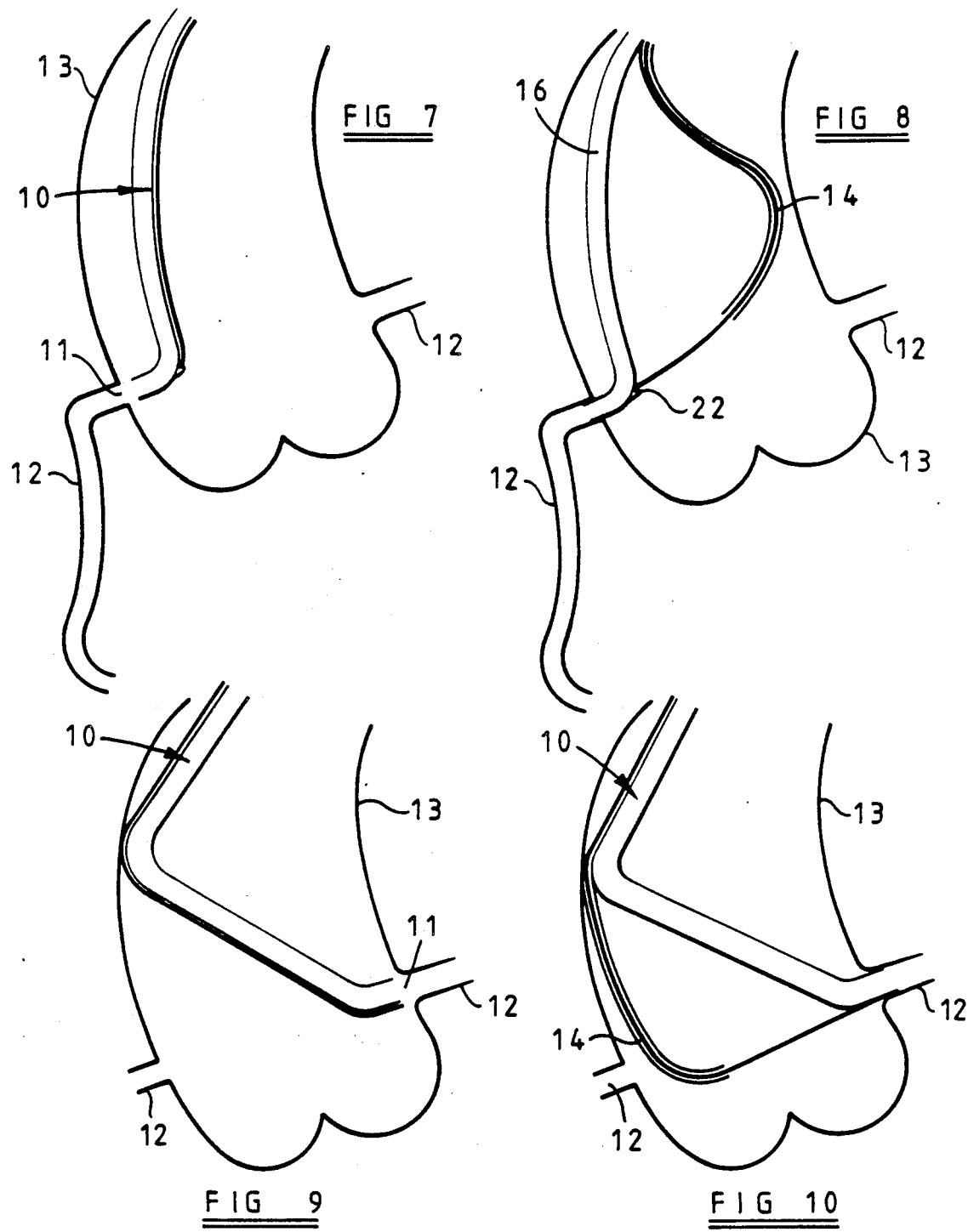

SUPPORT SYSTEM FOR CATHETER

BACKGROUND OF THE INVENTION

1. Field of the Invention

This invention relates to a support system for a catheter, specifically for a guiding catheter used in coronary treatment.

It was particularly devised for use in the technique of percutaneous transluminum coronary angioplasty (PCTA) which involves the passage of a balloon catheter inside a larger and firmer guiding catheter to the coronary artery.

One role of the guiding catheter is to provide a channel for monitoring of blood pressure and for the injection of X-ray contrast material. Another role is to provide support for manipulation of the balloon catheter, especially during the actual crossing of tight stenoses or blockages.

2. Description of the Prior Art

Currently available guiding catheters are larger and firmer versions of angiographic catheters which are primarily designed to give contrast injections for X-ray purposes, rather than to provide anchorage at the site of entry to the coronary artery. Many instances of failure of PTCA procedures are due to this lack of support by the guiding catheter.

The problem of insecure anchorage may also affect other angioplasty devices which have been proposed, for example cutters, lasers and drills.

It has been proposed in U.S. Pat. No. 4,813,930 to Elliott to provide an angioplasty guiding catheter having a primary lumen to act as a guide for a balloon catheter or similar device and a secondary lumen in which one or more bracing wires are provided. The secondary lumen is apertured at a position spaced from the distal end of the catheter and endwise pressure can be exerted on the wire or wires which may project in one or more loops so as to be braced against the wall of a vessel and to hold the catheter in place.

However, the use of either one or two wires is objectionable in that the pressure exerted on the vessel wall may cause damage at the point or points of bracing contact because the wire or wires tend to embed in the wall of the vessel. Similarly, damage may be caused when withdrawing the catheter. Where only a single bracing wire is provided, there is a danger that the catheter may be insufficiently braced against lateral movement and may suddenly give way if a lateral force is exerted upon it by the insertion or manipulation of for example a balloon catheter.

Furthermore, the position at which the catheter is braced is spaced from the catheter at the distal end so that the tip itself of the catheter is not supported.

SUMMARY OF THE INVENTION

It is an object of the present invention to provide a guiding catheter having improved support.

According to the invention there is provided a catheter having proximal and distal ends, the catheter comprising a main lumen, a secondary lumen and a linearly incompressible, flexible elongate element slidably disposed within the secondary lumen, the main lumen and secondary lumen being integrally connected together throughout a proximal portion of the length of the catheter and being separated throughout a distal portion, the elongate element being anchored at the distal end of the catheter, and operating means being provided at the proximal end of the catheter to exert endwise force on the elongate element and to cause said separated portion of the secondary lumen to move away from the main lumen, whereby the catheter may be braced against opposed walls of a vessel to retain it in position.

The elongate element may comprise a strip of incompressible metal or plastics tape. Preferably, it comprises a stainless steel strip.

The strip may be slightly arcuate in cross-section. The concave side of the arcuate strip may face the primary lumen.

The operating means may comprise a manual slide secured to the elongate element and projecting from a slotted portion of the secondary lumen at the proximal end of the catheter.

BRIEF DESCRIPTION OF THE FIGURES OF THE DRAWINGS

Embodiments of the invention will now be described in more detail by way of example only with reference to the accompanying drawings in which:

FIG. 1 is a side elevational view of a distal end portion of a guiding catheter embodying the invention shown in a partly deployed condition;

FIG. 2 is a section on the line 2.2 of FIG. 1;

FIG. 3 is a section on the line 3.3 of FIG. 1;

FIG. 4 is a section on the line 4.4 of FIG. 1;

FIG. 5 is a longitudinal sectional view on an enlarged scale of a proximal end of the guiding catheter showing operating means;

FIG. 6 is a perspective view of the operating means shown in FIG. 5;

FIG. 7 and 8 are illustrations of the insertion and deployed conditions of a Judkins type right coronary catheter embodying the invention;

FIGS. 9 and 10 are similar views of a Judkins type left coronary catheter;

DETAILED DESCRIPTION OF THE PREFERRED EMBODIMENT

Figure 11:
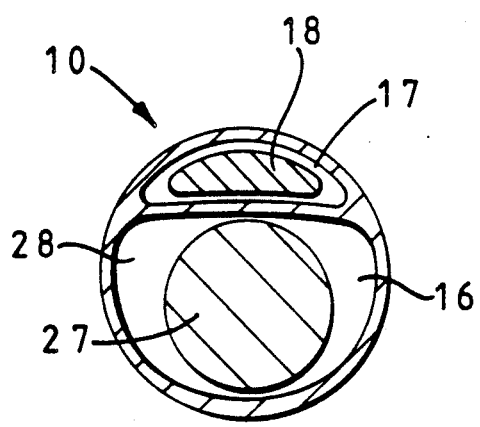
FIG. 11 is an enlarged sectional view of a guiding catheter similar to the section of FIG. 2, but shown in use.

The invention has been devised to provide active support to a guiding catheter used in for example PTCA procedures. Current guide catheters are based on those used for angiography, which do not need to be retained against any substantial outward thrust once positioned in the coronary orifice.

In balloon angioplasty, the distal end of the guiding catheter may be forced out of the coronary orifice as the operator attempts to advance the angioplasty balloon catheter.

Various techniques have currently been proposed to avoid this, mostly by wedging the tip of the guiding catheter deep inside the entrance of the coronary artery. This is often ineffective and can be hazardous as coronary blood flow may be reduced or damage may be caused to the osteum or entrance of the coronary artery by the forceful manoeuvre.

Although attempts have been made, for example in U.S. Pat. No. 4,813,930 to Elliott, to provide improved support for a guiding catheter, such proposals have not become generally accepted for the reasons outlined above.

Referring firstly to FIGS. 7–10 of the accompanying drawings, a guiding catheter generally indicated at 10 is positioned in conventional manner at the osteum 11 of a coronary artery 12, the aorta being indicated in diagramatic outline at 13. FIGS. 7 and 9 show the positioning of the guiding catheter.

In FIGS. 8 and 10, the catheter has been actively supported in the correct position by support means 14 to be described in more detail with reference to FIGS. 1-4.

The guiding catheter 10 has the section shown in FIG. 2 of the drawings throughout most of its length. It is made of conventional flexible biologically acceptable synthetic plastics material. It has a generally circular outer periphery 15 and a pair of passageways, the primary lumen 16 and a secondary lumen 17. As seen in FIG. 2, the primary lumen 16 is considerably larger in size than the secondary lumen 17. The secondary lumen carries an elongate flexible and linearly incompressible strip 18 which may be of any suitable metal or alloy of a biologically acceptable nature. A preferred material is stainless steel.

The strip 18 is arcuate with a concave surface facing towards the primary lumen 16. As will be seen, the primary lumen 16 and secondary lumen 17 form complementary segments of the generally circular cross-section guiding catheter 10.

The distal end portion of the catheter 10 has a slightly different formation. The partition wall 19 between the primary lumen 16 and secondary lumen 17 is split on a parting line 20 at the region of the section line 3.3 of FIG. 1. The distal portion generally indicated at 21 is such that the secondary lumen 17 is completely split from the primary lumen 16 of the catheter for a distance of approximately 50 mm. It will be seen that the end of the secondary lumen 17 is free from the primary lumen 16. However, the elongate incompressible flexible strip 18 is firmly secured at 22 at the distal end of the catheter to the main lumen 16. This arrangement constitutes the bracing means 14.

The proximal end of the catheter is shown in FIGS. 5 and 6 of the drawings. The elongate strip 18 has a rigidly secured slider 23 which projects through an opening 24 in the secondary lumen 17. The primary lumen 16 is secured and sealed at 25 to an end member 26 of generally known type. The arrangement is such that the strip 18 can slide within the secondary lumen 17 under control of the manual operating means such as the slider 23. However, since the distal end 22 is fixed securely to the main lumen 16 of the guiding catheter, any endwise force exerted on the incompressible strip 18 causes the secondary lumen 17 to separate from the primary lumen 16 in the region at the distal end portion where the two are separate. Separation only takes place in this region.

The effect of deployment in this manner is to brace the incompressible strip 18, covered by the secondary lumen 17 against an opposed wall of the vessel within which the catheter is located. This can be seen in FIGS. 7-10 of the drawings where the catheter is inserted in the heart. The distal end of the catheter is located in the atrium of the appropriate coronary artery and the strip 18 in its protective lumen 17 is braced against the opposed wall of the vessel.

The amount of separation of the two parts of the catheter can be controlled by the user by adjusting the amount of forward movement of the slider 23. Judgement is necessary to ensure that an adequate amount of bracing support is available without exerting undue force on the wall of the vessel. However, it will be appreciated that the secondary lumen 17 acts to protect the wall of the vessel from damage by the possibly sharp edges of the strip 18. Only a portion between the point of attachment 22 and the end of the secondary lumen 17 is exposed and this portion does not contact the wall.

The relatively broad secondary lumen 17, combined with the use of an incompressible bracing strip 18, provide resistance against lateral and rotational movement of the guiding catheter 10, in addition to spreading the loading on the vessel to reduce the risk of damage.

FIG. 11 of the drawings diagramatically illustrates the use of the guiding catheter to receive an inner catheter 27 such as a balloon catheter, to be inserted into the coronary artery 12 to clear a blockage. Since the primary lumen 16 is of non-circular cross-section, once the catheter 27 has been passed through it, a passageway 28 still exists to permit, for example, the monitoring of blood pressure or for the injection of contrast material for angiography.

When the procedure has been completed the inner catheter 27 can be withdrawn safely without dislodging the guiding catheter 10. The slider 23 is then gently withdrawn, causing the secondary lumen 17 of the catheter to move alongside the primary lumen 16 at the distal end as the elongate strip 18 is drawn back into the of the catheter can be withdrawn in the usual manner from the atrium of the coronary artery.

Although described in connection with holding the guiding catheter in position, the device may also be used to vary the orientation of the distal tip of the guiding catheter during attempts to engage the coronary osteum. This may be necessary in cases where there is a mismatch between the shape and size of the catheter and that of the aortic root. This may be particularly useful in the case shown in FIG. 9 of the drawings in positioning a Judkins type left coronary guiding catheter where the catheter tip is strongly angled. Upward and downward pointing of the catheter tip is difficult to achieve in conventional diagnostic or guiding catheters.

Since the catheter is supported to some extent by the guiding strip 18 incorporated in the secondary lumen, it may be possible to use a rather more flexible plastics material with less inner braiding than is currently used, reducing the overall thickness of the catheter wall. If necessary, a biologically acceptable coating may be added to the strip, for example a low friction plastics material such as PVC or PTFE to reduce friction inside the relatively tightly fitting secondary lumen 17.

Because the strip is of curved cross-section, it is unlikely to buckle under endwise loading necessary to deploy the bracing mechanism, especially as the strip is constrained by the secondary lumen. However, it still has flexibility sufficient to allow the catheter to be passed satisfactorily into the appropriate position when the system is not deployed.

Although described in connection with coronary procedures, it will be appreciated that the support system for the catheter may have other uses.

Again, although the illustrations here involve the use of Judkins type guiding catheters, the system may be incorporated into guiding catheters of any current or future design.

I claim:

1. A catheter having proximal and distal ends, the catheter comprising a primary lumen, a secondary lumen and a linearly incompressible, flexible elongate element slidably disposed within the secondary lumen, the main lumen and secondary lumen being integrally connected together throughout a proximal portion of the length of the catheter and being separated throughout a distal portion, the elongate element being anchored at the distal end of the catheter, and operating means being provided at the proximal end of the catheter to exert endwise force on the elongate element and to cause said separated portion of the secondary lumen to move away from the main lumen whereby the catheter may be braced against opposed walls of a vessel to retain it in position.

2. A catheter according to claim 1 wherein the elongate element comprises a strip of incompressible tape.

3. A catheter according to claim 2 wherein said strip has an arcuate cross-section.

4. A catheter according to claim 3 wherein said arcuate cross-section has a concave side facing the primary lumen.

5. A catheter according to claim 1 wherein the elongate element is of incompressible metal.

6. A catheter according to claim 5 wherein said metal is stainless steel.

7. A catheter according to claim 1 wherein said elongate element comprises incompressible plastics tape.

8. A catheter according to claim 1 wherein said operating means comprises a manual slide secured to the elongate element, a slotted portion is provided in said secondary lumen at the proximal end of the catheter and said manual slide projects from said slotted portion.

9. A catheter according to claim 1 wherein the external cross-section of the catheter is substantially circular throughout said proximal portion in which the primary lumen and secondary lumen are integrally connected together.

10. A catheter according to claim 1 wherein the internal cross-section of said primary lumen is of laterally enlarged noncircular cross-section.

* * * * *